United States Patent [19]

Leone et al.

[11] Patent Number: 5,505,700
[45] Date of Patent: Apr. 9, 1996

[54] ELECTRO-OSMOTIC INFUSION CATHETER

[75] Inventors: James E. Leone; Stephen M. Rowland, both of Miami, Fla.

[73] Assignee: Cordis Corporation, Miami Lakes, Fla.

[21] Appl. No.: 259,534

[22] Filed: Jun. 14, 1994

[51] Int. Cl.⁶ .................................................. A61M 31/00
[52] U.S. Cl. ........................................................ 604/96
[58] Field of Search ......................... 604/96, 101, 20–22; 606/191–194

[56] References Cited

U.S. PATENT DOCUMENTS

| | | | |
|---|---|---|---|
| 4,411,648 | 10/1983 | Davis et al. | 604/21 |
| 4,636,195 | 1/1987 | Wolinsky . | |
| 5,047,028 | 9/1991 | Qian . | |
| 5,087,243 | 2/1992 | Avitall . | |
| 5,236,413 | 8/1993 | Feiring . | |
| 5,256,141 | 10/1993 | Gencheff et al. | 604/101 |
| 5,286,254 | 2/1994 | Shapland et al. . | |
| 5,334,154 | 8/1994 | Samson et al. | 604/96 |
| 5,344,402 | 9/1994 | Crocker | 604/96 |

FOREIGN PATENT DOCUMENTS 9116945  11/1991  WIPO .
9119529  12/1991  WIPO .

*Primary Examiner*—C. Fred Rosenbaum
*Assistant Examiner*—Manuel Mendez
*Attorney, Agent, or Firm*—Lockwood, Alex, Fitzgibbon & Cummings

[57] ABSTRACT

An infusion catheter is provided for delivering treatment fluids including medicaments, drugs, pharmaceuticals, cancer treatment agents and the like directly to a location within a living body such as within a vessel or body cavity. Electro-osmotic infusion is carried out by iontophoretic and/or iontohydrokinesis procedures. The infusion catheter includes both an internal electrode and an integral electrode, both of which are components of or closely associated with a distal portion of the catheter itself. When electrically joined to an EMF source, the electrodes are oppositely charged. The treatment fluid or components of the treatment fluid have an electrical charge which is the same as the internal electrode, as a result of which the medicament moves away from the internal electrode and to the body component being treated.

19 Claims, 3 Drawing Sheets

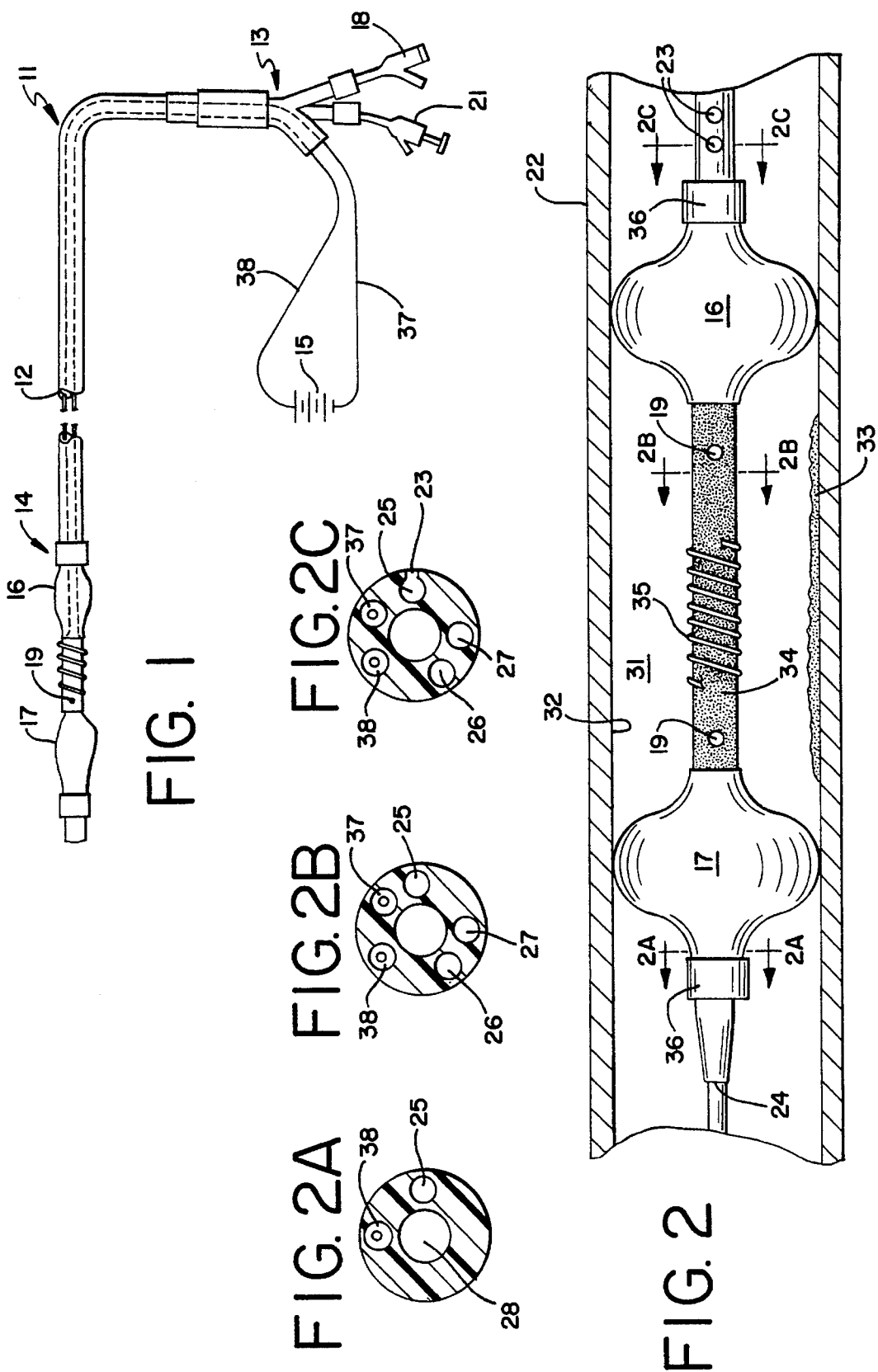

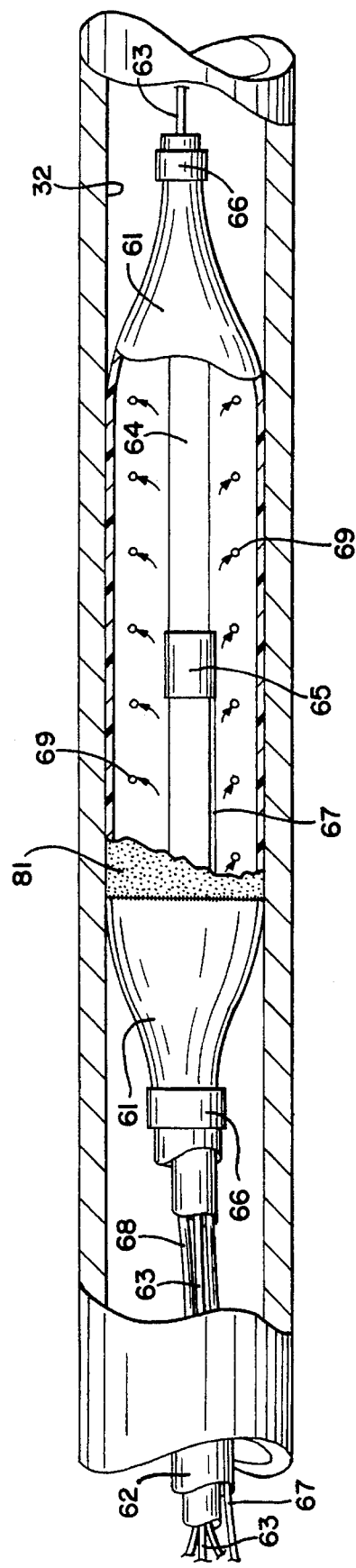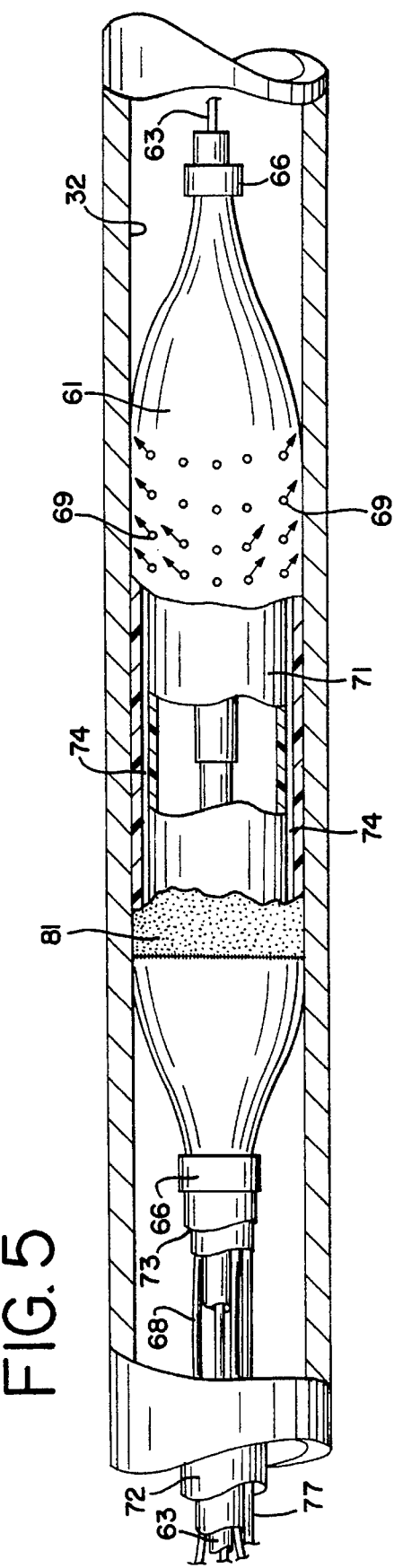

ELECTRO-OSMOTIC INFUSION CATHETER

BACKGROUND AND DESCRIPTION OF THE INVENTION

The present invention generally relates to medical catheters for delivery of medicaments directly to treatment sites within a living body. More particularly, the invention relates to infusion catheters having electro-osmotic features which incorporate electrical charges and voltage drops to facilitate the localized medicament delivery. The electrodes across which the voltage drop is experienced are components of the catheter itself, and any need for external electrodes is eliminated.

Medicaments can be administered to living bodies by a number of approaches, including topical administration, intravenous administration, injection into body tissue via hypodermic needles and the like, and oral administration. In some instances, it is important to minimize the contact of the medicament with areas of the body other than the specific area targeted for treatment. For example, such an approach reduces the dilution effect by having to distribute the medicament to portions of the body that do not require the treatment. Direct delivery to the target site also minimizes the chance of side effects by restricting the drug administration to the precise site in need of treatment. In other instances, the area to be treated is not readily accessible in the absence of fully invasive surgery, such as when it is desired to treat the interior of a blood vessel or other body vessel or cavity.

Over the years, infusion catheter systems have been developed in order to deliver medication, pharmaceuticals, drugs or other medicaments to a localized site by the use of injection from a distal portion of a catheter such as an intravenous catheter or the like. One difficulty that has been encountered in connection with infusion catheter systems is the development of streaming. In many infusion catheter systems, a liquid medicament is injected under pressure, such as by way of a hypodermic syringe or a pumping device, from out of a distal end portion of an intravascular catheter. Often, this entails injection pressures which can be relatively high when compared with a possibly delicate condition of a diseased or damaged vessel or the like such that there is a concern that vessel trauma can occur by high pressure streaming, particularly when the exit port is directed toward the vessel wall or the like. Accordingly, such approaches have the possible disadvantage of being somewhat mechanically traumatic. Also, such direct injection approaches can be less controlled, especially in the sense of delivering medication over a preselected period of time.

Approaches have been taken or proposed in order to improve these types of mechanical infusion catheter systems. Included in this regard are systems which are designed to selectively and locally deliver a drug or medicament to internal body tissue, which systems include a perforated, permeable or semi-permeable material through which the drug or medicament selectively passes. Exemplary in this regard is Shapland et al PCT International Publication No. WO 91/19529, incorporated by reference hereinto. This publication also generally mentions that passage through such a membrane can be facilitated by utilizing so-called iontophoresis technology for this type of transdermal medicament delivery. Iontophoresis technology uses an electrical potential or current across a semi-permeable barrier to drive ionic medicaments toward the target treatment site. Iontophoresis can also include the concept of dragging non-ionic medicaments across the semi-permeable barrier by incorporating same within an ionic solution or carrier. At times, particularly when water is the carrier, this latter approach can be referred to as iontohydrokinesis.

Another approach in this regard is found in Feiring U.S. Pat. No. 5,236,413, incorporated by reference hereinto. Both this patent and the Shapland et al PCT publication propose using iontophoresis or iontohydrokinesis as described in these references by the use of an electrode which is external to the patient's body. By this latter approach, an internal electrode is positioned inside of a permeable balloon. An electric field is developed between this internal electrode and an external electrode or electrodes such as patch or paddle electrodes that are positioned on the outside surface of the body. In accordance with this approach, medication is delivered into the balloon and weeps through the minute pores of the balloon during generation of the electric field between the internal electrode and the external or return electrode.

In accordance with the present invention, the undesirable aspects of having to pass the electrical current through body tissue because of the potential set up between an internal electrode and an external return electrode are eliminated. Instead, an internal electrode is combined with another electrode which is positioned on the catheter itself, which is considered to be integral with respect to the catheter. By this approach, any external catheter is eliminated. The physician need only insert the electro-osmotic infusion catheter in accordance with customary catheter insertion techniques. The self-contained approach of the present invention is easier to use and less complicated for the physician. The step of having to properly place the external return electrode is completely eliminated. Also eliminated is the possibility of creating stray electric fields within the body, inasmuch as the electric circuit is confined to a specific area at the distal portion of the catheter itself and typically within the vessel itself. The medicament distribution is more uniform, and the medicament delivery itself is more efficient by proceeding in accordance with the present invention.

In summary, the present invention is an electroosmotic infusion catheter and procedure for delivery of medicaments or treatment fluids to a location within a living body. The catheter carries out localized treatment of internal body tissue, such as re-stenosis reduction and the treatment of cancers by localized delivery of drugs to a tumor location, for example. The distal portion of the catheter includes one or more balloon components to define a treatment location and/or to treat diseased or injured areas. Delivery is facilitated by the use of an electrical circuit which includes an internal electrode and an integral electrode that is positioned along the catheter at its distal portion, which electrical circuit influences the path of travel of the medicament to direct same toward the area being treated.

It is a general object of the present invention to provide an improved infusion catheter and method of using same.

Another object of the present invention is to provide an improved infusion catheter that carries out localized treatment of internal body tissues.

Another object of this invention is to provide an improved infusion catheter which uses an integral electrical circuit confined to the distal end portion of the infusion catheter.

Another object of the present invention is to provide an improved infusion catheter and procedure using electro-osmotic principles to deliver medicaments to locations within a living body that are accessible through catheterization procedures.

Another object of the present invention is to provide an improved catheterization procedure which effects electroosmotic infusion of medicaments to localized sites within a living body in accordance with a self-contained approach which avoids the need for an external electrode.

Another object of this invention is to provide an improved infusion catheter and medicament infusion procedure by a self-contained electrical circuit approach which is of enhanced efficiency and uniformity with respect to medicament delivery.

Another object of this invention is to provide an improved infusion catheter and medicament infusion procedure which avoid the creation of stray electric fields within the body.

Another object of the present invention is to provide an improved infusion procedure and catheter which reduces restenosis development after an angioplasty procedure by directing treatment fluid to a localized area at the site of an angioplasty treatment.

Another object of this invention is to provide an improved infusion procedure and catheter for localized treatment of cancers.

Another object of this invention is to provide an improved infusion catheter and treatment procedure wherein catheter balloons generally flank a treatment area at which medicaments under the influence of an integral voltage drop are directed to that treatment location.

Another object of the present invention is to provide an improved infusion catheter and procedure which virtually eliminate potentially disruptive or damaging streaming of medicament flow onto the treatment site.

These and other objects, features and advantages of the present invention will be clearly understood through a consideration of the following detailed description.

BRIEF DESCRIPTION OF THE DRAWINGS

The invention will be further elucidated in the following description with reference to the drawings in which:

FIG. 1 is an elevational view, partially broken away, of a preferred infusion catheter in accordance with the present invention;

FIG. 2 is a detailed view of the distal portion of the catheter shown in FIG. 1, located within a body vessel, shown in cross-section;

FIG. 2A is a cross-sectional view along the line 2A—2A of FIG. 2;

FIG. 2B is a cross-sectional view along the line 2B—2B of FIG. 2;

FIG. 2C is a cross-sectional view along the line 2C—2C of FIG. 2;

FIG. 4 is a view, partially in cross-section and partially broken away, of a further embodiment of a catheter, shown within a body vessel; and FIG. 5 is a view, partially in cross-section and partially broken away, of an additional embodiment of a catheter, shown within a body vessel.

DESCRIPTION OF THE PARTICULAR EMBODIMENTS

Figure 3:
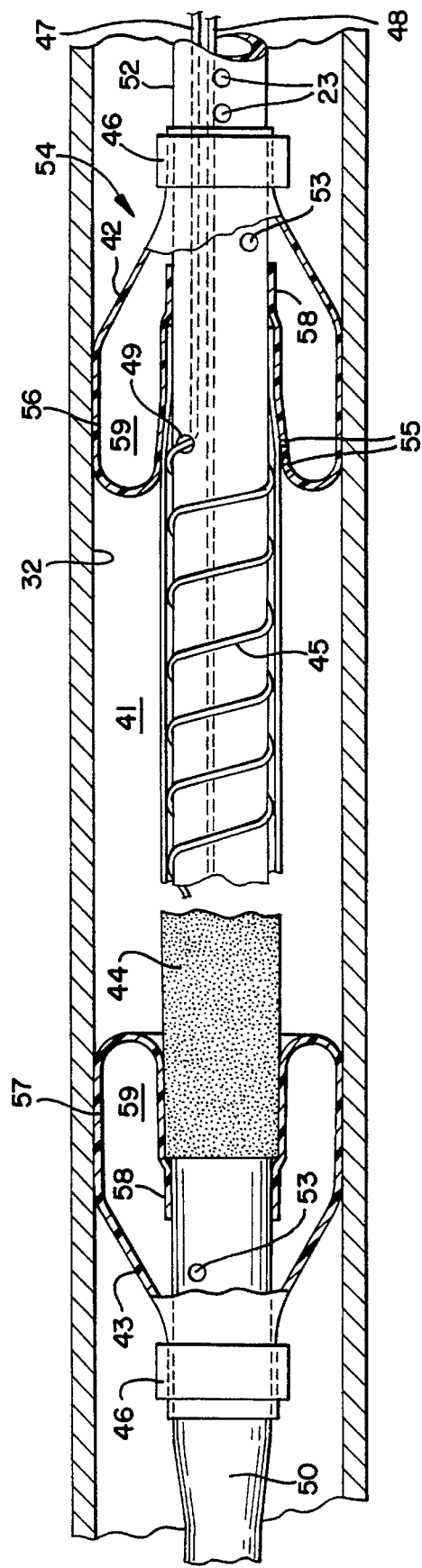
FIG. 3 is a view, partially in cross-section and partially broken away, of another embodiment of a catheter, shown within a body vessel.

An infusion catheter, generally designated as 11, is generally illustrated in FIG. 1. The catheter includes a multi-lumen catheter tube 12, a proximal portion, generally designated as 13, and a distal portion generally designated as 14. Also included is electrical circuitry including multiple electrodes wired to an electrical source 15.

Distal portion 14 includes a pair of inflatable balloons 16, 17, shown in a generally deflated state in FIG. 1. These balloons are in communication with one or more lumens within the catheter tube. A fluid injector assembly 18 of generally known construction passes inflation fluid through these lumen(s) to the inflatable balloons 16, 17. If desired, multiple fluid injection assemblies can be provided. A separate lumen within the catheter tube 12 communicates one or more ejection port(s) 19 to an infusion assembly 21 for directing medicament from the proximal portion to the distal portion of the infusion catheter. The administration of medicament in this regard can be as a precisely measured dosage from a hypodermic syringe, or as a flow of medicament, which can be a recirculating flow if desired.

In the embodiment which is illustrated in greater detail in FIG. 2, balloon members 16 and 17 are shown in an inflated state and in engagement with an inside wall of a vessel 22 such as a blood vessel or the like. Description herein will be with respect to blood vessels; nevertheless, it will be understood that the invention is applicable to use with respect to other vessels or internal body components.

In the embodiment illustrated in FIG. 2, blood within the vessel 22 has a general flow from right to left. In order to reduce the chance of ischema development or other undesirable effects, a suitable perfusion system is provided. The illustrated system includes blood perfusion ports 23 and a blood perfusion outlet opening 24, which can take the form of slits, ports or the like. A perfusion lumen 25 is included to permit this flow through the distal portion of the infusion catheter. A lumen such as that illustrated at 26 is provided for inflating and deflating either or both of the inflatable balloons 16, 17. A separate lumen 27 communicates the infusion assembly 21 with injection port(s) 19 which operate as drug infusion port(s). A central lumen 28 can be provided as illustrated in order to accommodate a guidewire (not shown), for example, or for some other purpose that requires a lumen passageway through the catheter.

It will be appreciated that, with the balloon inflated as illustrated in FIG. 2, an annular chamber 31 is defined therebetween. When medicaments pass through the port(s) 19, they pass into annular chamber 31 to contact vessel wall 32 and for treatment of, for example, a diseased area 33 thereof.

Movement of the medicament to the vessel wall 32 and any diseased area 33 thereon is enhanced by operation of the electrodes and their associated electrical source 15. After the medicament is infused either out of port(s) 19 or through pores or osmotic passageways of catheter treatment length 34, a voltage is applied such that an ionically charged medicament fluid forces the fluid to move away from a like-charged internal electrode component 35 and toward the vessel wall. The charge associated with the internal electrode 35 is developed by a voltage drop between internal electrode 35 and one or more integral electrode(s) 36. Internal electrode 35 and integral electrode(s) 36 are connected to opposite poles of the electrical or EMF source through suitable wires (preferably insulated) 37, 38 respectively. While the electrodes 35, 36 are illustrated as either a coiled wire or a wire band, either electrode component could take on either configuration and can include additional or alternate configurations such as longitudinally directed veins, conductive meshes, conductive coatings applied by deposition or the like, and components that function as radiopaque markers. It will be appreciated that the electric field associated with this infusion catheter is contained within the area of the distal portion of the infusion catheter and does not stray away from vessel 22 itself. It will also be appreciated, of course, that the internal electrode component 35 is charged oppositely of the integral electrode(s).

The infusion catheterization procedure carried out in accordance with the present invention includes inserting and feeding the infusion catheter in a manner suitable for catheterization of the particular location which is to be treated in accordance with this aspect of the invention. When properly positioned at the treatment site, the balloons 16, 17 are inflated until they engage the vessel wall 32. This step is particularly non-traumatic to the vessel being treated because of the small contact area of the balloons and the relative softness of the narrow balloons. In addition, in many treatment situations according to this aspect of the invention, the balloons remain spaced away from the diseased or damaged area that is to be treated.

Medicament is infused into the chamber by way of infusion ports or other suitable porous outlet into the chamber. Voltage is applied, and the resulting charge on the internal electrode is the same as that on the medicament or medicament carrier, thereby providing the impetus for the medicament to move away from the internal electrode and to and/or into the vessel wall. There is also a tendency for the charged medicament to move generally toward the integral electrode(s) which are along the distal portion of the catheter. As a result, the medicament migrates to the vessel wall at a rate faster than through the operation of only normal osmotic pressure.

The embodiment of FIG. 3 is generally similar to that of FIG. 1. Included is an annular chamber 41 defined along vessel wall 32 between inflatable balloon(s) 42, 43. A catheter treatment length generally coincides with the treatment chamber 41 and can include a generally cylindrical membrane through which the medicament can diffuse. It also prevents electrical shorting to the vessel wall. In this particular embodiment, the catheter treatment length includes a porous membrane 44 which covers internal electrode 45. The treatment fluid passes through the porous membrane after it flows out of infusion port(s) 49. In the illustrated embodiment, the coiled internal electrode 45 passes through an infusion port 49. Iontophoresis wire lead 47 connects the internal electrode 45 to the electrical source, and wire lead 48 electrically connects integral electrode(s) 46 to the source of EMF. Perfusion can proceed between blood perfusion ports 23 and a distal tip 50 having a perfusion lumen (not shown).

Distal portion 54 of multi-lumen catheter tube 52 further includes inflatable balloons 56, 57. Balloons 56, 57 are mounted in a somewhat "inside out" fashion. More specifically, each balloon has at least one of its mounting legs 58 located beneath or inside of the inflatable body 59 of the balloon. In this manner, the balloon overlaps the mounted leg. When inflated as illustrated in FIG. 3, this balloon structure helps to define distinct edges to the annular treatment chamber 41. When the overlapping balloon body 59 totally or partially covers medicament infusion port 49 as illustrated in FIG. 3, this can assist in preventing streaming of the medicament when it is delivered under pressure into the chamber 41 by virtue of the stream being deflected by the balloon body 59 lying generally thereover. In other instances, when medicament is to be emitted through the balloon(s) 56, 57, outlets through the balloon wall can be within the portion of the body of the balloon which engages or faces the catheter shaft. Drilled holes 55 are illustrated in this regard as an alternative site for medicament entry into the annular chamber 41.

Typically, each balloon will be inflated by means of an inflation port 53 which can be in communication with a dedicated lumen or the drug delivery lumen as desired, depending upon the particular medicament delivery arrangement that is utilized. The folded over balloon arrangement illustrated in FIG. 3 is also useful in even further reducing the likelihood of trauma to the vessel being treated. The overlapping relationship provides an especially soft or resilient contact area. It also provides a longitudinal expansion location of the balloon which is not provided by other balloon structures wherein both legs are beyond the balloon body and are not covered by the balloon body.

The procedure for using the infusion catheter as illustrated in FIG. 3 is generally the same as that accomplished with the infusion catheter of FIG. 2. In addition, the folded "inside out" balloons help in sealing the covered balloon leg onto the catheter directly under the balloon inasmuch as balloon pressure forces this leg onto the catheter body. The procedure can also include initially directing the fluid flow toward the catheter body itself rather than radially outwardly as in other procedures.

In the embodiment of FIG. 4, a single inflatable balloon 61 is secured to the catheter body, inside of which balloon an internal electrode 65 is positioned. Integral or external electrodes 66 are outside of balloon 61. Multi-lumen catheter tube 62 includes a lumen for passage of a guidewire 63 therethrough, when one is utilized. Catheter tube 62 further provides for passage of leads such as insulated wire lead 68, which provides electrical communication between an EMF source and integral electrode(s) external of the inflatable balloon 61. Also provided in this regard is another lead such as insulated wire lead 67 providing electrical communication between the EMF source and the internal electrode 65, which can also function as a marker band in accordance with known principles. Furthermore, a length 64 of the catheter tube which is within the balloon 61 can include a conductive outer skin, treatment or covering which renders it conductive and accepting of the same charge as that of the medicament and/or of its carrier, as well as of the internal electrode band 65, when provided. Band 65 can itself be eliminated provided the length 64 exhibits adequate electrical conductivity to accomplish the objectives of the invention.

As with the other embodiments, the medicament or its carrier having a charge of the same polarity as that of the internal electrode 64 and/or 65 is forced to migrate away from the internal electrode location. In this instance, migration is to the inside surface of inflatable balloon 61, which is porous. Thus, the charged medicament or medicament with its charged carrier, in the form of electrically charged particles, molecules, cells or the like, is forced to migrate from the like-charged surface of the catheter and to the outer, cylindrical surface of the catheter and pass through its pores 69 so as to engage and thereby treat the vessel wall 32. In this embodiment, the medicament is a liquid substance or is included within a liquid substance which is the substance that initially expands and maintains expansion of the porous balloon 61. This liquid is injected into the porous balloon with sufficient pressure such that the balloon contacts the vessel wall. Passage through the pores is accomplished principally by operation of the electric field generated between the internal electrode and the integral, external electrode(s).

With reference to FIG. 5, this is a variation on the general approach illustrated in FIG. 4. Once again, an external porous balloon 61 is positioned at the treatment site. In this instance, an electrically conductive and non-porous inner balloon 71 is positioned within the porous balloon 61. A suitable insulated wire lead 77 provides the communication between this inner balloon 71 and the EMF source. Integral electrodes 66 external of the balloons are in communication with this EMF source by way of the insulated wire lead 68. The balloon expansion liquid enters the multi-lumen catheter 72 in accordance with generally known approaches in order to fill the electrically conductive inner balloon 71 to expand same and the porous balloon 61 as well. A separate passageway or lumen 73 provides for passage of the medicament to be subjected to iontophoresis or iontohydrokinesis to a plenum chamber which is a generally annular passageway 74 between porous balloon 61 and non-porous conductive balloon 71. The medicament flows into this passageway 74 and out of the pores 69 by virtue of the like charge relationship between the medicament liquid and the inner balloon 71. Conductivity of the balloon can be accomplished by various approaches, including metallic deposition and/or electrical components such as a foil, mesh or fine wire system associated with balloon 71, whether on its inside or outside surface or embedded with the balloon material itself.

In a variation on the embodiments of FIG. 4 and FIG. 5, a porous membrane 81 can be positioned over the external balloon in order to even more carefully control the delivery of the medicament therethrough and to the vessel wall 32. This membrane, when added, is non-conductive. It is also possible that the membrane, in effect, replace the porous inflated balloon in the embodiment of FIG. 5. In addition, the porous membrane could be positioned over the balloon of the FIG. 4 embodiment. In that instance, it would further be possible to provide this porous balloon as a conductive component in addition to or in place of the internal electrode 65 of that embodiment.

The present invention avoids having pressure alone direct medicament to the treatment site. Accordingly, a less mechanically traumatic operation is practiced when compared with previous approaches. The invention also achieves a much more controlled manner of medication delivery over a preselected period of time. The invention can also be used to effect drug release by electroporation, which is the electrical breakdown of cells which contain substances such as hemolytic compounds, genes and the like. This enables normal vessel activity and healing at the treatment site.

The integral electrode approach in accordance with this invention has the advantage of being more efficient in the delivery of the medicaments, and the medicament delivery is more uniform when compared with prior art approaches. The invention has the further advantage of not creating stray electrical fields within the body, which fields would have the potential of affecting heart, brain or nerve performance, or the development of like side effects. Also avoided is interference with recording equipment by avoiding ground loops that can disturb testing devices. Also, the self-contained aspect makes the use of the device easier and less complicated. There is no need to attempt to properly place an external electrode.

In the embodiments using a microporous membrane positioned over the electrode having the same charge as the medicament or its carrier, possible electrical shorting of the electrode to the vessel wall is prevented while still allowing free flow of the liquid therapeutic substance through the membrane. The membrane also further assists in controlling or preventing streaming of liquid medicament with the resultant possibility of vessel wall trauma.

Preferably, the wire leads used in accordance with the invention are made of highly electrically conductive materials. Silver and/or silver chloride are exemplary in this regard. Pure silver is a preferred material.

It will be understood that the embodiments of the present invention which have been described are illustrative of some of applications of the principles of the present invention. Various modifications may be made by those skilled in the art without departing from the true spirit and scope of the invention.

We claim:

1. An infusion catheter for delivery of treatment fluid to a location within a living body, the catheter comprising:

an elongated tubular catheter assembly having a proximal portion which remains outside of the living body when in use, the catheter assembly also having a distal portion which is inserted into the living body when in use;

at least one inflatable balloon member at said distal portion of the catheter assembly, said balloon member being in fluid-passing communication with said proximal portion of the catheter assembly;

a tubular treatment length of said catheter assembly positioned along said distal portion of the catheter assembly, said treatment length having an infusion passageway in fluid-passing communication with said proximal portion of the catheter assembly;

an electrical circuit associated with said catheter, said electrical circuit having an internal electrode and an integral electrode, both of said internal electrode and integral electrode being positioned along said distal portion of the catheter assembly and on opposite sides of said balloon member;

said internal electrode is at said treatment length, and treatment fluid which passes out of said infusion passageway for contact with the living body is electrically charged; and said electrical circuit provides an electrical charge to said internal electrode which is the same as that of said electrically charged treatment fluid, said electrical circuit providing said electrical charge after said electrically charged treatment fluid has passed out of said infusion passageway.

2. The infusion catheter in accordance with claim 1, wherein at least two said balloon members are included, said internal electrode is located between said balloon members, and said integral electrode is distal of the distal-most of the balloon members.

3. The infusion catheter in accordance with claim 1, wherein at least two said balloon members are included, said internal electrode is located between said balloon members, and said integral electrode is proximal of the proximal-most of the balloon members.

4. The infusion catheter in accordance with claim 1, further including at least two of said balloon members, said internal electrode is located between said balloon members, and two of said integral electrodes are included, one being distal of the distal-most balloon member, and another being proximal of the proximal-most balloon member.

5. The infusion catheter in accordance with claim 1, wherein said internal electrode is within said balloon member, and said integral electrode is outside of said balloon member.

6. The infusion catheter in accordance with claim 5, wherein two of said integral electrodes are provided outside of said balloon member, each on opposite sides of said balloon member.

7. The infusion catheter in accordance with claim 1, wherein said infusion passageway includes an infusion port.

8. The infusion catheter in accordance with claim 1, wherein said infusion passageway includes a porous membrane.

9. The infusion catheter in accordance with claim 1, wherein said infusion passageway includes a porous membrane positioned over an infusion port.

10. The infusion catheter in accordance with claim 1, wherein said infusion passageway includes pores through said balloon member.

11. The infusion catheter in accordance with claim 1, wherein said infusion passageway includes an annular passageway internal of pores of said balloon member.

12. The infusion catheter in accordance with claim 11, further including an internal balloon member radially positioned within said balloon member, said internal balloon member being electrically conductive and comprising at least a component of said internal electrode.

13. The infusion catheter in accordance with claim 1, further including blood perfusion passageways through said distal portion of the catheter assembly for passage of blood and other body fluids through said distal portion of the catheter assembly when said balloon member is expanded into engagement with a vessel of the living body being treated.

14. The infusion catheter in accordance with claim 1, wherein said integral electrode has an electrical charge which is opposite to that of said internal electrode and of said treatment fluid.

15. The infusion catheter in accordance with claim 1, wherein said balloon member includes a mounting leg that is secured to a catheter tube of the distal portion of the catheter assembly, said mounting leg being located radially under said balloon member, thereby defining said balloon member as having an external balloon surface that is opposed to and engages said catheter tube along a location spaced generally axially away from said mounting leg.

16. The infusion catheter in accordance with claim 15, further including one or more holes in said balloon, which holes generally face said catheter tube.

17. An infusion catheter for delivery of treatment fluid to a location within a living body, the catheter comprising:

an elongated tubular catheter assembly having a proximal portion which remains outside of the living body when in use, the catheter assembly also having a distal portion which is inserted into the living body when in use;

two inflatable balloon members at said distal portion of the catheter assembly, said balloon members being in fluid-passing communication with said proximal portion of the catheter assembly;

a treatment length of said distal portion of the catheter assembly, said treatment length having an infusion passageway in fluid-passing communication with said proximal portion of the catheter assembly;

an electrical circuit associated with said catheter, said electrical circuit having an internal electrode and an integral electrode, both of said internal electrode and integral electrode being positioned along said distal portion of the catheter assembly, said internal electrode being at a location on said catheter between said balloon members, and said integral electrode being at a location on said catheter which is on a side of one of said balloon members that is opposite to said location of the internal electrode;

said internal electrode contacts said treatment length, and treatment fluid which passes out of said infusion passageway is electrically charged; and said electrical circuit imparts an electrical charge to said internal electrode which is the same as that of said electrically charged treatment fluid while said integral electrode has an electrical charge which is opposite to that of said electrically charged treatment fluid, said electrical circuit providing said electrical charge after said electrically charged treatment fluid has passed out of said infusion passageway.

18. The infusion catheter in accordance with claim 17, wherein each said balloon member includes a mounting leg that is secured to a catheter tube of the distal portion of the catheter assembly, said mounting leg being located radially under said balloon member, thereby defining said balloon member as having an external balloon surface that is opposed to and engages said catheter tube along a location spaced generally axially away from said mounting leg.

19. The infusion catheter in accordance with claim 18, further including one or more holes in said balloon, which holes generally face said catheter tube.

* * * * *